United States Patent
Hua et al.

(10) Patent No.: US 12,424,317 B2
(45) Date of Patent: *Sep. 23, 2025

(54) SYSTEMS, DEVICES, AND METHODS FOR REVISING OR SUPPLEMENTING ROM-BASED RF COMMANDS

(71) Applicant: ABBOTT DIABETES CARE INC., Alameda, CA (US)

(72) Inventors: Xuandong Hua, Mountain View, CA (US); Jean-Pierre Cole, Tracy, CA (US); Martin Fennell, Concord, CA (US); Theodore J. Kunich, Pleasanton, CA (US); Lane Westlund, Munich (DE); Arni Ingimundarson, Munich (DE)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,291

(22) Filed: Aug. 2, 2023

(65) Prior Publication Data

US 2024/0071611 A1    Feb. 29, 2024

Related U.S. Application Data

(63) Continuation of application No. 17/569,062, filed on Jan. 5, 2022, now Pat. No. 11,763,941, which is a
(Continued)

(51) Int. Cl.
*G16H 40/63* (2018.01)
*A61B 5/00* (2006.01)
(Continued)

(52) U.S. Cl.
CPC .......... *G16H 40/63* (2018.01); *A61B 5/0015* (2013.01); *A61B 5/14532* (2013.01);
(Continued)

(58) Field of Classification Search
CPC .................................................. G06F 19/3406
(Continued)

(56) References Cited

U.S. PATENT DOCUMENTS 6,877,063 B1    4/2005  Allegrucci et al.
6,973,522 B1    12/2005 Takahashi
(Continued)

FOREIGN PATENT DOCUMENTS

CN    101840373 A      9/2010
GB    2 424 294         9/2006
WO    WO 00/78210 A1   12/2000

OTHER PUBLICATIONS

Ilkun, Olesya, and Sihem Boudina. "Cardiac dysfunction and oxidative stress in the metabolic syndrome: an update on antioxidant therapies." Current pharmaceutical design 19.27 (2013): pp. 4806-4817. (Year: 2013).*
(Continued)

*Primary Examiner* — Satish Rampuria
(74) *Attorney, Agent, or Firm* — ONE LLP

(57) ABSTRACT

Systems, devices, and methods are provided that enable the revision of RF command handling software stored in ROM, and that enable to supplementation of RF command handling software stored in ROM. Examples of the systems, devices, and methods make use of a lookup data structure stored within writable non-volatile memory.

18 Claims, 8 Drawing Sheets

Related U.S. Application Data continuation of application No. 16/662,728, filed on Oct. 24, 2019, now Pat. No. 11,250,949, which is a continuation of application No. 14/945,149, filed on Nov. 18, 2015, now Pat. No. 10,497,473.

(60) Provisional application No. 62/081,851, filed on Nov. 19, 2014.

(51) Int. Cl.
    *A61B 5/145*     (2006.01)
    *G06F 13/16*     (2006.01)
    *G06F 13/42*     (2006.01)

(52) U.S. Cl.
    CPC .......... *G06F 13/16* (2013.01); *G06F 13/4282* (2013.01); *A61B 5/14503* (2013.01); *A61B 5/14546* (2013.01)

(58) Field of Classification Search
    USPC ................................................ 717/168–178
    See application file for complete search history.

(56) References Cited

U.S. PATENT DOCUMENTS

| | | | |
|---|---|---|---|
| 7,080,245 | B2 | 7/2006 | Ballard et al. |
| 7,809,347 | B2 | 10/2010 | Yancey |
| 8,850,421 | B2* | 9/2014 | Proud .................... H02J 50/70 717/172 |
| 9,509,402 | B2 | 11/2016 | Ryan et al. |
| 9,795,328 | B2* | 10/2017 | Taub .................... A61B 5/6849 |
| 10,188,333 | B2 | 1/2019 | Kamath et al. |
| 11,020,031 | B1* | 6/2021 | Simpson ............ A61B 5/14539 |
| 12,226,239 | B2* | 2/2025 | Williams ........... A61B 5/14532 |
| 2001/0048361 | A1 | 12/2001 | Mays et al. |
| 2003/0100331 | A1 | 5/2003 | Dress et al. |
| 2006/0193375 | A1 | 8/2006 | Lee |
| 2006/0242383 | A1 | 10/2006 | Chen et al. |
| 2007/0083713 | A1 | 4/2007 | Torrini et al. |
| 2008/0139910 | A1 | 6/2008 | Mastrototaro et al. |
| 2008/0282022 | A1 | 11/2008 | Gonikberg et al. |
| 2009/0299152 | A1 | 12/2009 | Taub et al. |
| 2009/0327650 | A1 | 12/2009 | Neuerburg |
| 2010/0045465 | A1 | 2/2010 | Brauker et al. |
| 2010/0060422 | A1 | 3/2010 | Van Nest et al. |
| 2010/0205422 | A1 | 8/2010 | Shao et al. |
| 2010/0324392 | A1 | 12/2010 | Yee et al. |
| 2011/0082484 | A1 | 4/2011 | Saravia et al. |
| 2011/0106126 | A1 | 5/2011 | Love et al. |
| 2011/0125040 | A1 | 5/2011 | Crawford et al. |
| 2011/0190603 | A1 | 8/2011 | Stafford |
| 2011/0191044 | A1 | 8/2011 | Stafford |
| 2011/0193704 | A1 | 8/2011 | Harper et al. |
| 2011/0213225 | A1* | 9/2011 | Bernstein ............... G16H 40/63 600/309 |
| 2011/0319729 | A1 | 12/2011 | Donnay et al. |
| 2011/0320787 | A1 | 12/2011 | Dieffenderfer et al. |
| 2012/0078278 | A1 | 3/2012 | Bales, Jr. et al. |
| 2012/0197222 | A1 | 8/2012 | Donnay et al. |
| 2012/0284498 | A1 | 11/2012 | Chou |
| 2013/0067186 | A1 | 3/2013 | Pronovost et al. |
| 2013/0116524 | A1 | 5/2013 | Cole et al. |
| 2014/0012116 | A1* | 1/2014 | Okuyama .......... A61B 5/14532 600/347 |
| 2014/0081107 | A1 | 3/2014 | Cole et al. |
| 2014/0088454 | A1 | 3/2014 | Mack |
| 2014/0124384 | A1* | 5/2014 | Gerber ............... G01N 27/3272 204/403.01 |
| 2019/0173885 | A1 | 6/2019 | Kamath et al. |
| 2020/0037939 | A1 | 2/2020 | Castagna et al. |
| 2023/0389844 | A1* | 12/2023 | Johnson ............. A61B 5/14865 |

OTHER PUBLICATIONS

Miller, Kellee M., et al. "Evidence of a strong association between frequency of self-monitoring of blood glucose and hemoglobin A1c levels in T1D exchange clinic registry participants." Diabetes care 36.7 (2013): pp. 2009-2014. (Year: 2013).*

Bode, Bruce W., et al. "Advances in hemoglobin A1c point of care technology." Journal of Diabetes Science and Technology 1.3 (2007): pp. 405-411. (Year: 2007).*

Klonoff, David C., et al. "Continuous glucose monitoring: an endocrine society clinical practice guideline." The Journal of Clinical Endocrinology & Metabolism 96.10 (2011): pp. 2968-2979. (Year: 2011).*

Tonyushkina, Ksenia, and James H. Nichols. "Glucose meters: a review of technical challenges to obtaining accurate results." Journal of diabetes science and technology 3.4 (2009): pp. 971-980. (Year: 2009).*

Facchinetti, Andrea, et al. "Real-time improvement of continuous glucose monitoring accuracy: the smart sensor concept." Diabetes care 36.4 (2013): pp. 793-800. (Year: 2013).*

WO, PCT/US2015/061374 ISR and Written Opinion, Mar. 4, 2015.

WO, PCT/US2014/067727 ISR and Written Opinion, Feb. 26, 2015.

Clarke, W. L., et al., "Closed-Loop Artificial Pancreas Using Subcutaneous Glucose Sensing and Insulin Delivery and a Model Predictive Control Algorithm: The Virginia Experience", Journal of Diabetes Science and Technology, 2009, vol. 3, No. 5, pp. 1031-1038.

Giokas, D. L., et al., "Programming Fluid Transport in Paper-Based Microfluidic Devices Using Razor-Crafted Open Channels", Analytical Chemistry, 2014, vol. 86, pp. 6202-6207.

Gong, S., et al., "Toward Smart Wireless Communications via Intelligent Reflecting Surfaces: A Contemporary Survey", IEEE Communications Surveys & Tutorials, 2020, vol. 22, No. 4, pp. 2283-2314.

Guan, H., et al., "An Analytical Model for Optimization of Programming Efficiency and Uniformity of Split Gate Source-Side Injection Superflash Memory", IEEE Transactions on Electron Devices, 2003, vol. 50, No. 3, pp. 809-815.

Ilkun, O., et al., "Cardiac Dysfunction and Oxidative Stress in the Metabolic Syndrome: an Update on Antioxidant Therapies", Current Pharmaceutical Design, 2013, vol. 19, No. 27, pp. 4860-4817.

Khan, Z., et al., "FPGA-Assisted Real-Time RF Wireless Data Analytics System: Design, Implementation, and Statistical Analyses", IEEE Access, 2020, vol. 8, pp. 4383-4396.

Lindroos, M., "On Glucose Metabolism in Patients With the m.3243A>G Mutation", Dissertation University of Turku, 2013, pp. 1-143.

Querlioz, D., et al., "Bioinspired Programming of Memory Devices for Implementing an Inference Engine", Proceedings of the IEEE, 2015, vol. 103, No. 8, pp. 1398-1416.

Sakata, S., et al., "Programming control of intelligent drug releases in response to single and binary environmental stimulation signals using sensor and electroresponsive hydrogel", Radiation Physics and Chemistry, 2007, vol. 76, pp. 733-737.

Speth, M., et al., "Effects of prolonged strenuous exercise on plasma levels of cardiac troponins and natriuretic peptides in healthy female individuals", Abstracts: Congress of Clinical Chemistry and Laboratory Medicine, 2005, pp. A87-A88.

Tiwari, P. K., et al., "Integrated Wireless Sensor Network for Large Scale Intelligent Systems", International Conference on Advances in Computing, Communications, and Informatics (ICACCI), 2013, pp. 1849-1854.

Tomic, J., "The relationship between glucose metabolism byproduct, D-lactate, and vascular endothelial cell dysfunction and possible role in diabetes", Dissertation University of Saskatchewan, 2013, pp. 1-98.

Volek, J. S., et al., "The Art and Science of Low Carbohydrate Living", Beyond Obesity, 2011, pp. 1-197.

Winkelman, J. W., et al., "The Fiscal Consequences of Central vs Distributed Testing of Glucose", Clinical Chemistry, 1994, vol. 40, No. 8, pp. 1628-1630.

CA, 2,926,198 Examiner's Report, Feb. 5, 2024.

(56) References Cited

OTHER PUBLICATIONS

CN, 201480064824.3 First Office Action, Sep. 3, 2018.
EP, 14866144.0 Supplementary Search Report, Jun. 15, 2017.

* cited by examiner

SYSTEMS, DEVICES, AND METHODS FOR REVISING OR SUPPLEMENTING ROM-BASED RF COMMANDS

CROSS-REFERENCE TO RELATED APPLICATIONS

The present application is a continuation of U.S. patent application Ser. No. 17/569,062, filed Jan. 5, 2022, now U.S. Pat. No. 11,763,941, which is a continuation of U.S. patent application Ser. No. 16/662,728, filed Oct. 24, 2019, now U.S. Pat. No. 11,250,949, which is a continuation of U.S. patent application Ser. No. 14/945,149, filed Nov. 18, 2015, now U.S. Pat. No. 10,497,473, which claims priority to and the benefit of U.S. Provisional Patent Application Ser. No. 62/081,851, filed Nov. 19, 2014, all of which are incorporated by reference herein in their entireties for all purposes.

FIELD

The subject matter described herein relates to systems, devices, and methods for revising the execution of RF commands stored in ROM and/or supplementing the RF commands stored in ROM, for example, with respect to medical devices used in an analyte monitoring environment.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. Accordingly, needs for improved analyte monitoring systems, devices, and methods exist.

SUMMARY

A number of systems have been developed for the automatic monitoring of the analyte(s), like glucose, in a bodily fluid of a user, such as in the blood, interstitial fluid ("ISF"), dermal fluid, or in other biological fluid. Some of these systems include a sensor that can be at least partially positioned "in vivo" within the user, e.g., transcutaneously, subcutaneously, or dermally, to make contact with the user's bodily fluid and sense the analyte levels contained therein. These systems are thus referred to as in vivo analyte monitoring systems.

The sensor is generally part of a sensor control device that resides on (or in) the body of the user and contains the electronics and power source that enable and control the analyte sensing. The sensor control device, and variations thereof, can be referred to as a "sensor control unit," an "on-body electronics" device or unit, an "on-body" device or unit, or a "sensor data communication" device or unit, to name a few.

The analyte data sensed with the sensor control device can be communicated to a separate device that can process and/or display that sensed analyte data to the user in any number of forms. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. The reader device can be a dedicated use device, a smart phone, a tablet, a wearable electronic device such as a smart glass device, or others.

In vivo analyte monitoring systems can be broadly classified based on the manner in which data is communicated between the reader device and the sensor control device. One type of in vivo system is a "Continuous Analyte Monitoring" system (or "Continuous Glucose Monitoring" system), where data can be broadcast from the sensor control device to the reader device continuously without prompting, e.g., in an automatic fashion according to a broadcast schedule. Another type of in vivo system is a "Flash Analyte Monitoring" system (or "Flash Glucose Monitoring" system or simply "Flash" system), where data can be transferred from the sensor control device in response to a scan or request for data by the reader device, such as with a Near Field Communication (NFC) or Radio Frequency Identification (RFID) protocol.

In vivo analyte monitoring systems can be differentiated from "in vitro" systems that contact a biological sample outside of the body (or rather "ex vivo") and typically include a meter device that has a port for receiving an analyte test strip carrying bodily fluid of the user, which can be analyzed to determine the user's blood sugar level.

Both in vitro and in vivo systems can utilize locally stored software to perform a number of measurement, data collection, data analysis, communication, and other application related functions. This software can be stored, at least in part, in non-volatile memory within the device. One such non-volatile memory is read-only memory (ROM), which provides advantages in cost, power efficiency, and reliability, among others. Software that is stored in ROM is electrically and physically designed into the memory layout during the semiconductor manufacturing process, i.e., the software is permanently coded in the ROM. The software therefore cannot be altered after the semiconductor device has been manufactured. The introduction of a software revision can only be accomplished by redesigning the semiconductor device, producing a revised layout, assembling new photolithography masks, and fabricating entirely new semiconductor chips, which is a lengthy and expensive process. It may also require those semiconductor devices that were already assembled to be discarded.

However, analyte monitoring applications can be complex and continually evolving as ever more research and resources are devoted to improving the health and lifestyle of the patients. These applications are also subject to governmental regulations that can be introduced, changed, or interpreted in ways that require modifications to the operation of the analyte monitoring devices. The introduction of revisions to ROM-based software code are therefore a significant concern.

Described herein are a number of example embodiments of systems, devices, and methods that can allow the providers of analyte monitoring devices to supplement, disable, or revise existing RF command handling software that is, e.g., hardcoded within the ROM of a semiconductor device, without requiring the fabrication of new devices altogether. Many of these example embodiments are described with respect to an analyte monitoring environment, but can also be applied in other environments without limitation (both within and outside of the healthcare industry).

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Figure 1:
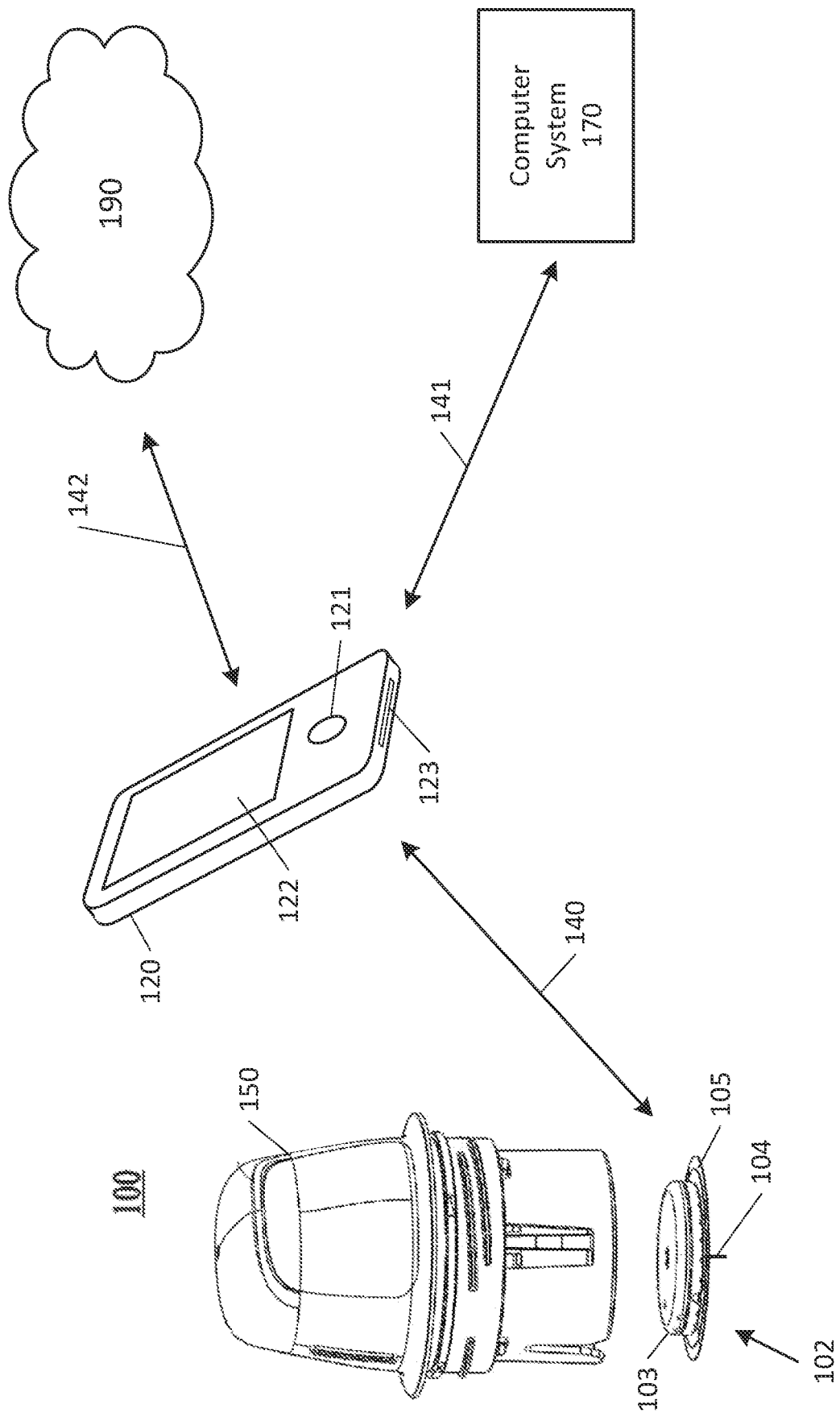
FIG. 1 is a high level diagram depicting an example embodiment of an analyte monitoring system for real time analyte (e.g., glucose) measurement, data acquisition and/or processing.

An example embodiment of an in vivo analyte monitoring system 100 with which the embodiments described herein can be used is depicted in the illustrative view of FIG. 1. Here, system 100 includes a sensor control device 102 and a reader device 120 that can communicate with each other over a local wireless communication path (or link) 140, which can be uni-directional or bi-directional. The communications sent across link 140 contain digital messages in a frame format (which includes packets) and can be based on a Near Field Communication (NFC) protocol (including an RFID protocol), Bluetooth or Bluetooth Low Energy (BTLE) protocol, Wi-Fi protocol, proprietary protocol, or others. Reader device 120 is also capable of wired, wireless, or combined communication over communication paths (or links) 141 and 142 with other systems or devices, such as a computer system 170 (e.g., a server for a website, a personal computer, a tablet, and the like) or cloud-based storage 190.

Other embodiments of sensor control device 102 and reader device 120, as well as other components of an in vivo-based analyte monitoring system that are suitable for use with the system, device, and method embodiments set forth herein, are described in U.S. Patent Application Publ. No. 2011/0213225 (the '225 Publication), which is incorporated by reference herein in its entirety for all purposes.

Figure 2A:
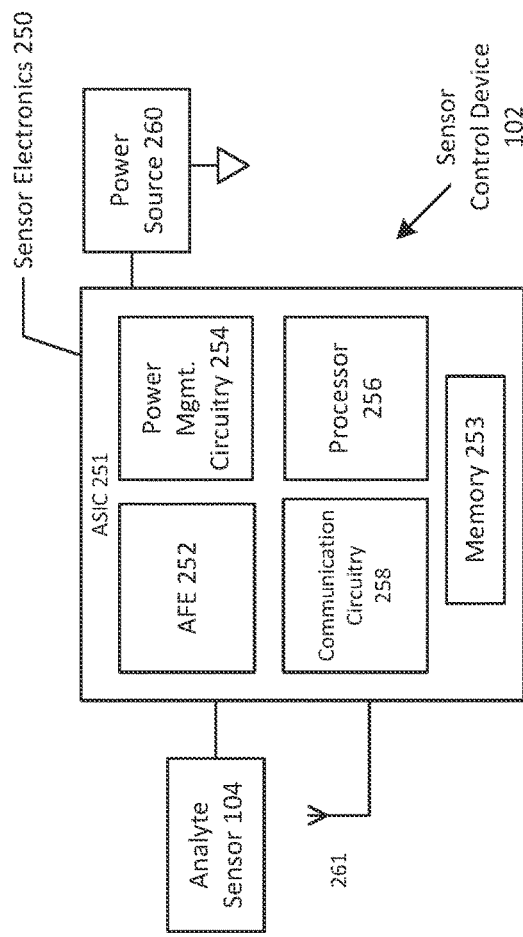
FIGS. 2A-C are block diagrams depicting example embodiments of a sensor control device.
Figure 2B:
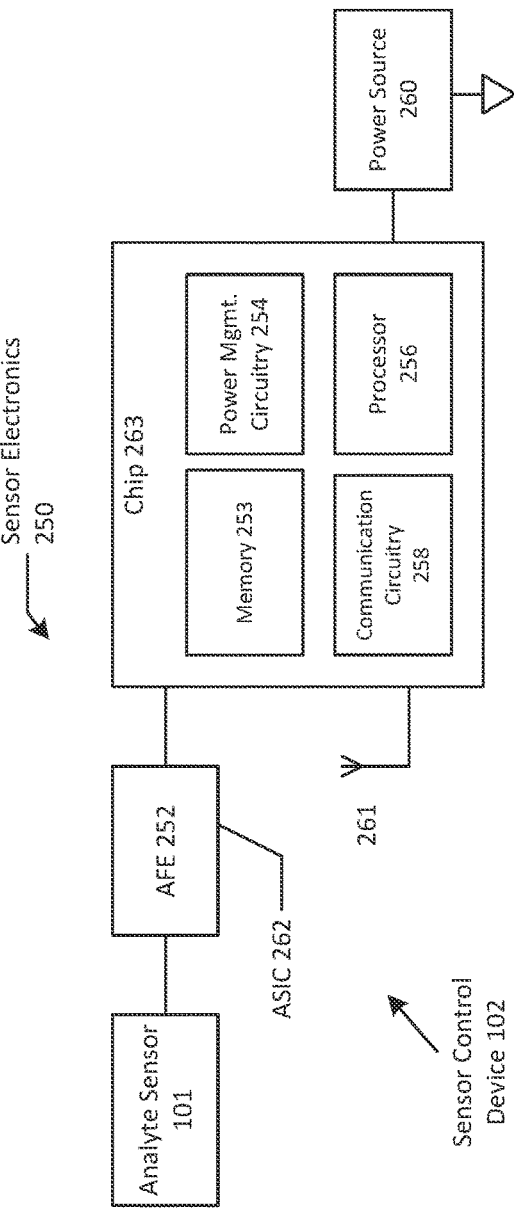

Sensor control device 102 can include a housing 103 containing in vivo analyte monitoring circuitry and a power source 260 (shown in FIGS. 2A-B). Referring to FIG. 1, the in vivo analyte monitoring circuitry is electrically coupled with an analyte sensor 104 that extends through a patch 105 and projects away from housing 103. An adhesive layer (not shown) can be positioned at the base of patch 105 for attachment to a skin surface of the user's body. Other forms of attachment to the body may be used, in addition to or instead of adhesive. Sensor 104 is adapted to be at least partially inserted into the body of the user, where it can make contact with the user's bodily fluid and, once activated, used with the in vivo analyte monitoring circuitry to measure and collect analyte-related data of the user. Generally, sensor control device 102 and its components can be applied to the body with a mechanical applicator 150 in one or more steps, as described in the incorporated '225 Publication, or in any other desired manner.

In other embodiments, system 100 can include wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime.

As shown in FIG. 1, reader device 120 includes a display 122 to output information to the user and/or to accept an input from the user (e.g., if configured as a touch screen), and one optional user interface component 121 (or more), such as a button, actuator, touch sensitive switch, capacitive switch, pressure sensitive switch, jog wheel or the like. Reader device 120 can also include one or more data communication ports 123 for wired data communication with external devices such as computer system 170 (described below). Reader device 120 may also include an in vitro analyte meter, including an in vitro test strip port (not shown) to receive an in vitro analyte test strip for performing in vitro analyte measurements.

Computer system 170 can be used by the user or a medical professional to display and/or analyze the collected analyte data with an informatics software program. Computer system 170 may be a personal computer, a server terminal, a laptop computer, a tablet, or other suitable data processing device, and can be (or include) software for data management and analysis and communication with the components in analyte monitoring system 100.

The processing of data and the execution of software within system 100 can be performed by one or more processors of reader device 120, computer system 170, and/or sensor control device 102. For example, raw data measured by sensor 104 can be algorithmically processed into a value that represents the analyte level and that is readily suitable for display to the user, and this can occur in sensor control device 102, or it can occur in reader device 120 or computer system 170 after receipt of the raw data from sensor control device 102. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

As discussed above, reader device 120 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly may be capable of wireless communications similar to a smartphone. Other examples of wearable electronics include devices that are worn around or in the proximity of the user's wrist (e.g., a watch, etc.), neck (e.g., a necklace, etc.), head (e.g., a headband, hat, etc.), chest, or the like.

FIG. 2A is a block diagram depicting an example embodiment of sensor control device 102 having analyte sensor 104 and sensor electronics 250 (including analyte monitoring circuitry). Although any number of chips can be used, here the majority of sensor electronics 250 are incorporated on a single semiconductor chip 251 that can be a custom application specific integrated circuit (ASIC). Shown within ASIC 251 are certain high-level functional units, including an analog front end (AFE) 252, power management (or control) circuitry 254, processor 256, and communication circuitry 258 for communications between device 102 and reader device 120. In this embodiment, both AFE 252 and processor 256 are used as analyte monitoring circuitry, but in other embodiments either circuit (or a portion thereof) can perform the analyte monitoring function. Processor 256 can include one or more processors (e.g., two processors acting in concert), microprocessors, controllers, and/or microcontrollers.

A non-transitory memory 253 is also included within ASIC 251 and can be shared by the various functional units present within ASIC 251, or can be distributed amongst two or more of them. Memory 253 can be volatile and/or non-volatile memory. In this embodiment, ASIC 251 is coupled with power source 260, e.g., a coin cell battery. AFE 252 interfaces with in vivo analyte sensor 104 and receives measurement data therefrom, conditions the data signal, and outputs the data signal to processor 256 in analog form, which in turn uses an analog-to-digital converter (ADC) to convert the data to digital form (not shown) and then processes the data to arrive at the end-result analyte discrete and trend values, etc.

This data can then be provided to communication circuitry 258 for sending, by way of antenna 261, to reader device 120 (not shown) where further processing can be performed. Communication circuitry 258 can operate according to any of the wireless (e.g., NFC, Bluetooth, and Wi-Fi) communication protocols described herein, or any other desired communication protocol, depending on the selected manner of communication with reader device 120. In other embodiments communication circuitry 158 can be adapted for wired communication.

Figure 2C:
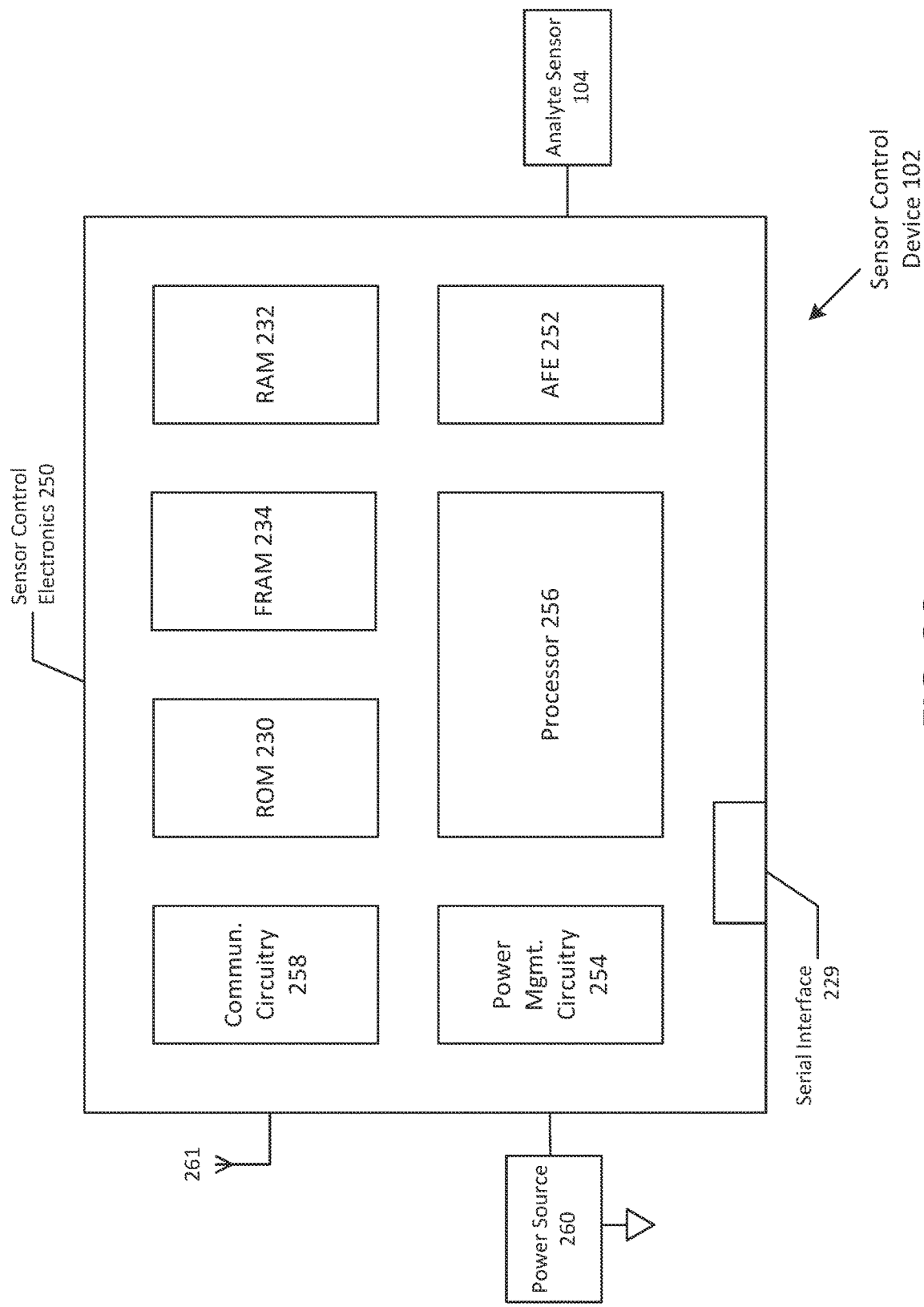

FIG. 2C is similar to FIG. 2B but instead includes two discrete semiconductor chips 262 and 263, which can be packaged together or separately. Here, AFE 252 is resident on ASIC 262. Processor 256 is integrated with power management circuitry 254 and communication circuitry 258 on chip 263. In one example embodiment, AFE 252 is combined with power management circuitry 254 and processor 256 on one chip, while communication circuitry 258 is on a separate chip. In another example embodiment, both AFE 252 and communication circuitry 258 are on one chip, and processor 256 and power management circuitry 254 are on another chip. Other chip combinations are possible, including three or more chips, each bearing responsibility for the separate functions described, or sharing one or more functions for fail-safe redundancy.

FIG. 2C is a block diagram depicting another embodiment of sensor control device 102, which can be implemented as one or more ASICs. As with the embodiments described with respect to FIGS. 2A-B, an analyte sensor 104, antenna 261, and a power source 260 are coupled with sensor electronics 250, which again includes AFE 252, power management circuitry 254, processor 256, and communication circuitry 258. Here, sensor electronics 250 are shown with the non-transitory memory divided into both volatile and non-volatile memory units (or portions). Specifically, sensor electronics 250 includes ROM 230 (non-volatile), random access memory (RAM) 232 (volatile), and ferroelectric RAM (FRAM) 234 (non-volatile). Other types of non-volatile memory can also be used, including, but not limited to, flash memory, magnetoresistive RAM (MRAM), erasable programmable read-only memory (e.g., EPROM or EEPROM), a hard disk, an optical disc, and a holographic memory.

In certain embodiments, part or all of the application software is stored within ROM 230, including the application (or other) software responsible for processing or handling received RF commands. As described herein, revisions to the RF command handling software can be stored to FRAM 234 during the board assembly or test phase (i.e., after fabrication and packaging of the semiconductor chips).

Also included with sensor electronics 250 is a serial interface 229. In certain embodiments, serial interface 229 is for serial testing and can be configured as a boundary scan interface linked to a boundary scan architecture that permits access to the internal circuitry of sensor electronics 250 that may not otherwise be accessible after sensor electronics 250 is assembled into a semiconductor package, or onto a larger printed circuit board (PCB), and the like. Serial interface 229 can permit the writing of new software to electronics 250, such as replacement code for code stored within ROM 230, as is described in further detail herein.

In certain embodiments, the boundary scan architecture can be a Joint Test Action Group (JTAG) architecture, or other architecture conforming to IEEE 1149.1 (Standard Test Access Port and Boundary Scan Architecture), although the boundary scan architecture is not limited to such. In one embodiment where serial interface 229 is in a JTAG configuration (not shown), interface 229 includes four externally accessible inputs and/or outputs (e.g., pins, pads, or connectors, and the like) that can be (or can be equivalent to) a Test Data In (TDI) input, a Test Data Out (TDO) output, a Test Clock (TCK) input, and a Test Mode Select (TMS) input. A Test Reset (TRST) can also optionally be included. TDI can be used for inputting any data or software (not necessarily test related) into the device and TDO can be used for outputting any data from the device. TCK can be used as a clock and TMS can be used to switch the architecture between various modes or state machine states. Together they can permit the serial advancement of data or software through a chain of internal registers (not shown) and into the internal circuitry and memory as needed.

Sensor electronics 250 depicted in FIG. 2C can be implemented as one single semiconductor chip or as multiple chips located on one or more PCBs. If implemented as multiple chips, the functions provided by each of AFE 252, power management circuitry 254, processor 256, communication circuitry 258, ROM 230, RAM 232, and FRAM 234 can be implemented on separate chips or can be dispersed such that each resides on more than one chip, or any combination readily recognized to those of ordinary skill in the art.

All of the elements of FIGS. 2A-C (e.g., processor 256, AFE 252, communication circuitry 258, memory 253, ROM 230, FRAM 234, RAM 232, power management circuitry 254, sensor 104, serial interface 229) can be configured to communicate with every other element directly (e.g., via a dedicated pathway or bus), indirectly (e.g., via one or more common or shared buses), or any combination of the two.

All or part of the RF command handling software for sensor control device 102 can be hardcoded, or permanently coded, within ROM 230 or another type of non-volatile memory. The systems, devices, and methods described herein can provide an efficient, flexible, and/or cost-effective pathway to revising or supplementing that software.

Embodiments of these systems, devices, and methods will be described with respect to an example implementation, namely, the revision, replacement, or supplementation of RF command handling software resident within ROM 230 of a sensor control device 102 used in an in vivo analyte monitoring environment. However, these embodiments can likewise be applied to other implementations, including, but not limited to: those in which the RF command handling software is resident within another type of non-volatile memory other than ROM; devices other than sensor control devices (e.g., readers, meters, etc.); in vitro analyte monitoring implementations, or hybrid implementations utilizing both in vivo and in vitro functionality; and other implementations outside of the medical field. In other words, the systems, devices, and methods described herein can be used in many implementations other than that of a sensor control device having ROM that is used in an in vivo analyte monitoring environment.

While not limited to such, the embodiments described are particularly suitable to implementation on ASICs where reprogramming of the software code and reconfiguration of the supporting hardware circuitry is much more difficult than in more flexible architectures, such as field-programmable gate arrays (FPGAs), programmable logic or programmable logic devices (PLDs). With sufficient volume, custom chips, in the form of ASICs, offer a very attractive proposition. ASICs may also be used sometimes because they enable circuits to be made that might not be technically viable using other technologies. They may offer speed and performance that would not be possible if discrete components were used. Conventional ASIC methodology relies on libraries of so-called, "standard cells." These libraries contain large numbers of pre-designed circuits (basic building blocks) that can be selected, mixed, rearranged, and re-used for different customers or applications. After the subset of cells is selected, they are frugally laid-out in the IC circuit space, adjacent appropriate other blocks, and are interconnected to construct more complex circuits within the integrated circuit in a space efficient (and therefore cost optimal) manner. Examples of digital ASIC standard cells include multi-BIT adders, multipliers, multiplexers, decoders, and memory blocks (look-up tables). Examples of analog ASIC standard cells include amplifiers, comparators, analog-to-digital, and digital-to-analog converters. ASICs may include mixed signal designs (ICs having both analog and digital circuitry on the same substrate).

In many embodiments, sensor control device 102 receives RF or wireless commands over communication path 140 from reader device 120. These commands can instruct sensor control device 102 to take certain actions. Several examples include a command to activate the onboard sensor 104, to retrieve information about sensor 104 for authentication purposes, to read collected data values from memory, to sense an analyte level of the user, and so forth.

Figure 3A:
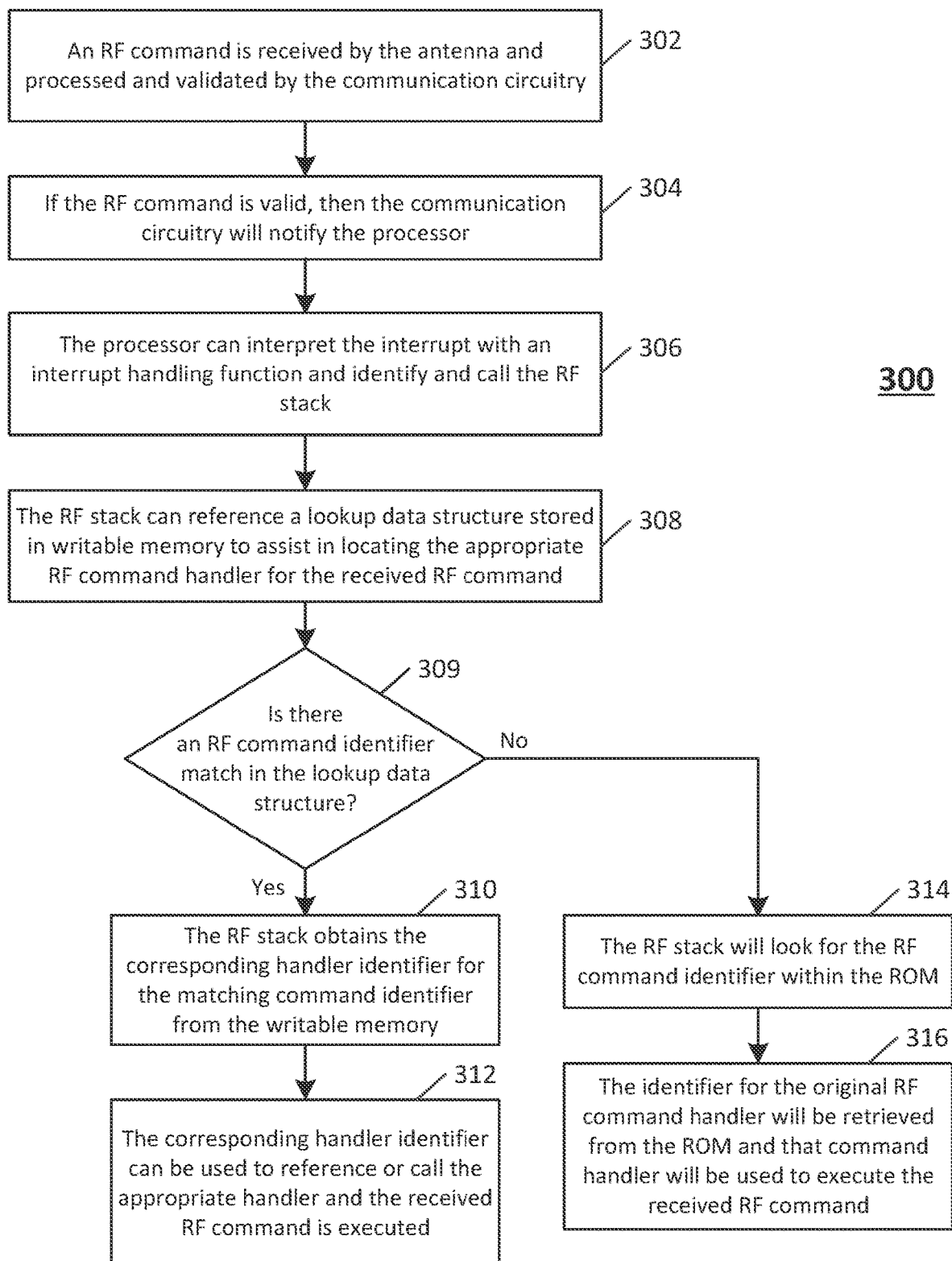
FIG. 3A is a flow diagram depicting an example embodiment of a method of determining the appropriate RF command handler to be used in executing a received RF command.

FIG. 3A is a flow diagram depicting an example embodiment of a method 300 performed by sensor control device 102 upon receiving an RF (or wireless) command. In many embodiments, method 300 can be coded in software either generally as part of the application program or as one or more software functions, and can be executed by processor 256 (and its variants). In embodiments herein, the application program may be referred to as application programming, application software or simply as programming or software, all of which are meant to indicate what is mainly permanent programming that exists in a device and that includes the numerous software functions.

Figure 3B:
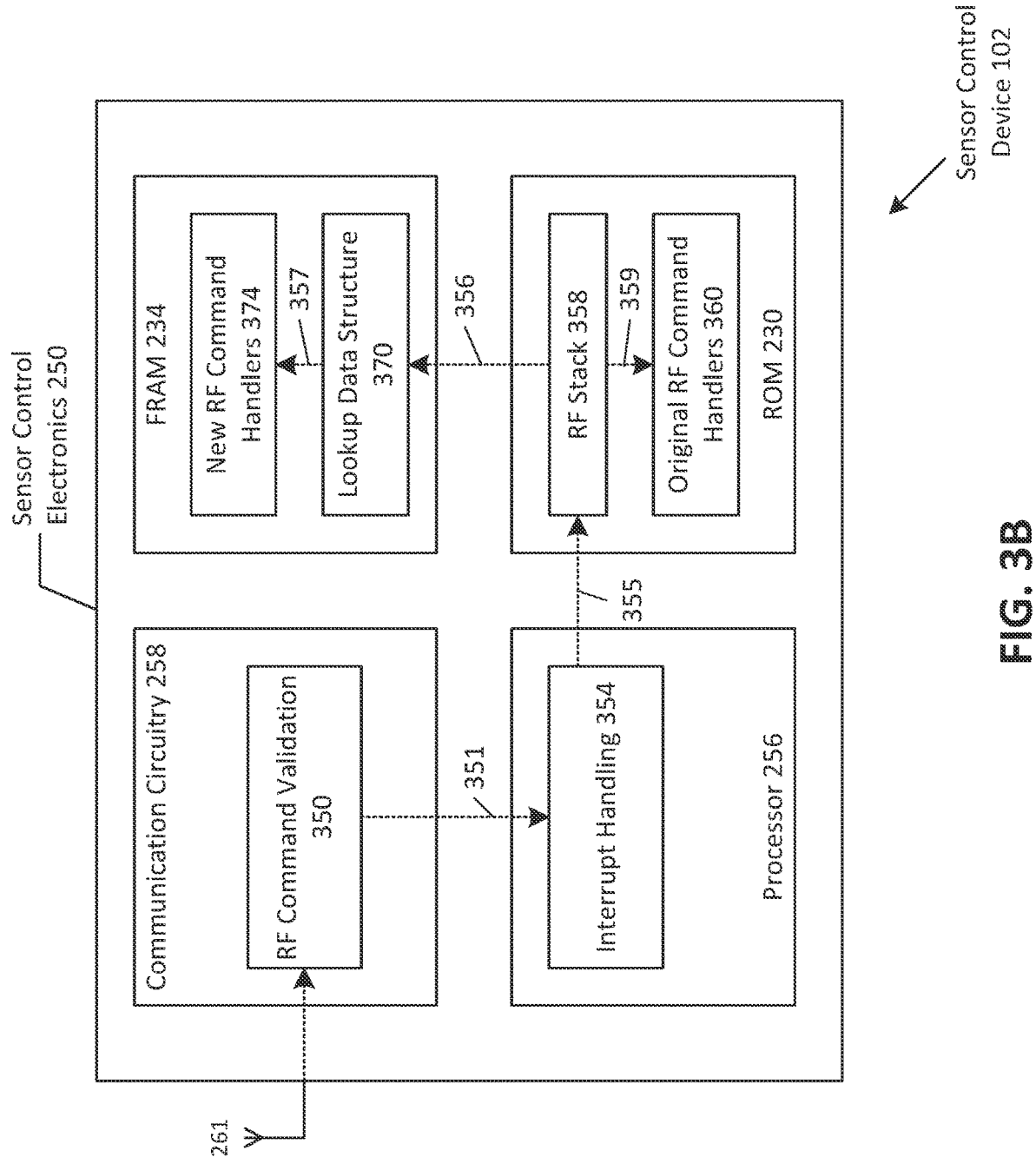
FIG. 3B is a conceptual block diagram depicting an example embodiment of a sensor control device at various stages during execution of an example method of determining the appropriate RF command handler to be used in executing a received RF command.

FIG. 3B is an illustrative diagram depicting an example embodiment of sensor control device 102 similar to that described with respect to FIG. 2C but omitting certain components for ease of illustration. The diagram of FIG. 3B will be used in conjunction with that of FIG. 3A to describe various stages of methods of processing the received RF command in a dynamic fashion, where sensor control device 102 uses software not originally hardcoded within ROM 230 to allow for a revised procedure for handling a particular RF command, or to allow for the handling of new RF commands beyond those that the original code was written to handle. The example embodiments described with respect to FIGS. 3A-B can be implemented with any embodiment of an analyte monitoring system 100 described herein.

At 302, an RF command is received by antenna 261 and processed and validated by communication circuitry 258. The RF command can be contained within a field of an RF transmission formatted according to the appropriate communication protocol (e.g., NFC, RFID, Bluetooth, Wi-Fi, etc.). The processing and validation of the received RF command can be performed by either hardware or software.

If the RF command is valid, then communication circuitry 258 will send an interrupt 351 (or other notification) to processor 256 at 304. If the RF command is not valid then no further action is taken. Processor 256 can interpret the interrupt with an interrupt handling function 354 and identify and call the appropriate software function for managing further processing of the received RF command at 306.

In this and other embodiments, the software function (or set of functions) that manages the further processing of the received RF commands (e.g., locating the appropriate handler) is referred to as RF stack 358, and can be hardcoded within ROM 230. Processor 256 issues a call 355 to RF stack 358 as shown in FIG. 3B. RF stack 358 is shown within ROM 230 to denote its place of storage in this embodiment, but would actually be executed by processor 256 during operation.

The term "function" is used broadly herein to encompass any program instruction, or sequence of instructions, that performs a specific task. In many embodiments, the function will be named and/or stored in a known location and the operating software will be capable of calling that function by its name or location. Various computer languages refer to software functions using different terminology such as routines, subroutines, procedures, methods, programs, subprograms, or callable units, each of which are within the scope of the term "function" as used herein. Likewise, the systems, devices, and methods described herein are not limited to any particular programming language.

Each RF command can be processed or handled by one or more software functions. These functions are referred to herein as handlers. One or more handlers can be stored in ROM 230 during fabrication and cannot be altered once stored. These one or more handlers are shown as original RF command handlers 360 in FIG. 3B. The term "original" is used because RF command handlers 360 are stored in ROM 230 during the ROM fabrication itself.

One or more additional RF command handlers can be stored in writable memory during a later (or different) stage of the manufacturing process. These handlers are referred to as new RF command handlers 374 and are stored in FRAM 234 in the embodiment of FIG. 3B. New RF command handlers 374 can be replacements for command handlers 360 (stored in ROM 230) that are revised to process a particular RF command in a different manner than was originally contemplated. Alternatively (or additionally), new RF command handlers 374 can include the programming to process new RF commands that the original sensor control device 102 did not have the capability to handle. In either case, the embodiments described herein can allow the functionality of sensor control device 102 to be altered without requiring new iterations of ROM 230 to be designed and fabricated, which saves numerous costs for the manufacturer.

In this context the terms "original" and "new" are used in a broad sense. The "original" RF command handler does not refer only to the very first iteration of ROM 230 that was developed or built, but can also refer to any subsequent iteration of ROM 230 including the latest one. Likewise, the "new" RF command handler does not refer only to the newest command handler or to a command handler that was only recently developed, but also any version of an RF command handler regardless of whether it is an earlier version or has been in existence for significant amount of time. The terms are used primarily to convey a distinction between those RF command handlers that were hardcoded within sensor control device 102 (i.e., original) and those RF command handlers that, regardless of reason, are written into sensor control device 102 to alter its functionality (i.e., new) from that provided solely by the original RF command handlers.

Referring back to FIG. 3A, after RF stack 358 is called by processor 256 at 306, RF stack 358 can reference a lookup data structure 370 stored in writable memory (e.g., FRAM 234) to assist in locating the appropriate RF command handler for the received RF command at 308. The referencing of lookup data structure 370 is depicted conceptually by arrow 356 in FIG. 3B.

Figure 4A:
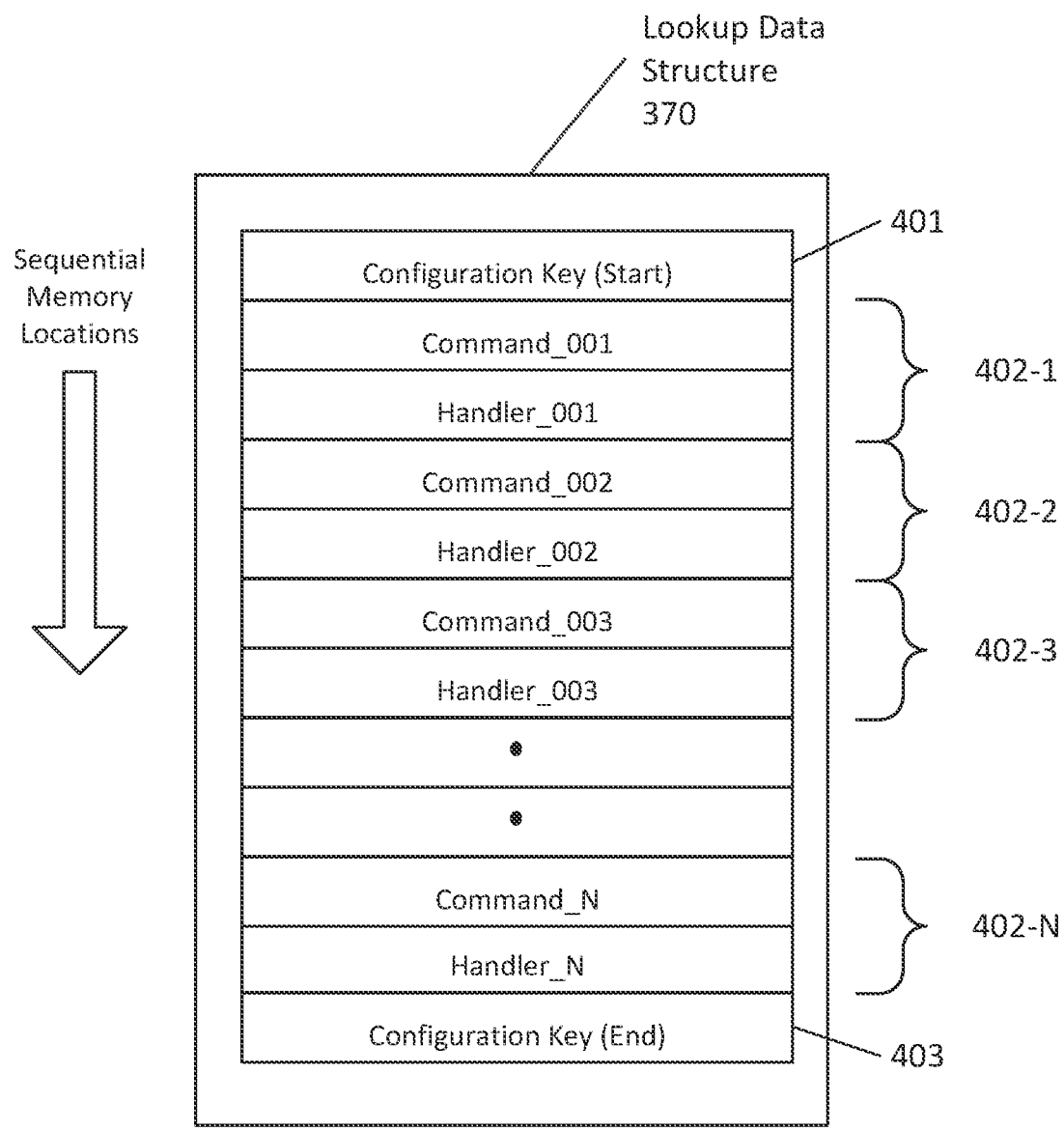
FIGS. 4A-C are block diagrams depicting example embodiments of a lookup data structure in human readable form.

Lookup data structure 370 can include identifications of some or all of the RF commands executable by sensor control device 102 along with identifications of their respective RF command handlers. An example embodiment of lookup data structure 370 is depicted in FIG. 4. In this embodiment, lookup data structure 370 is arranged sequentially in memory such that an identifier for each command is followed by the identifier for the handler responsible for executing that command. For example, the identifier for a first command (command_001) is followed by the identifier for the corresponding first command handler (handler_001) and this pair is labeled 402-1. Immediately following pair 402-1 is a second pair 402-2 that includes an identifier for a second command (command_002) and an identifier for the corresponding second command handler (handler_002). Lookup data structure 370 can include any number (N) of zero or more identifiers arranged in this fashion. Here, the ultimate pair is indicated by 402-N.

The command identifiers (command_001, command_002, etc.) can be any string of characters that is recognized within system 100 as identifying the RF command, e.g., an index, a name, or a memory pointer (e.g., an address). In some embodiments, the command identifier is a 16 bit number that can be represented by a string of four hexadecimal characters, e.g., 00A0, 1B2C, etc. Each of these command identifiers can be carried within a field of the encoded received wireless transmission and extracted from the received wireless transmission during the validation process. Other character lengths can be used as well.

The extracted command identifier can then be subsequently passed to RF stack 358, which, after being called at 308 (FIG. 3A), can perform a compare or match process between that received command identifier and those contained within lookup data structure 370 at 309. In the embodiment depicted in FIG. 4, RF stack 358 can proceed sequentially through lookup data structure 370 and can compare the received command identifier with the first command identifier. If the identifiers do not match, then RF stack 358 will advance two memory locations to the second command identifier and perform another compare. This process repeats until a match is found or the end of lookup data structure 370 is reached. The embodiments herein are not limited to this type of sequential marching through lookup data structure 370 and non-sequential or partially sequential techniques can be used as well.

Referring back to FIG. 3A, if a match is found, then RF stack 358 obtains the corresponding handler identifier for the matching command identifier at 310. In this embodiment, RF stack 358 will advance to the immediate next memory location that contains the handler identifier for the matching command. As with the command identifiers, the handler identifiers (handler_001, handler_002, etc.) can be any string of characters that is recognized within system 100 as identifying the RF command handler, e.g., an index, a name, or a memory pointer (e.g., an address). In some embodiments, the handler identifier is an address that identifies the location within memory (e.g., FRAM 234) where the handler software is stored. At 312, the handler identifier can be used to reference or call the appropriate handler and the received RF command is executed. For example, RF stack 358 can perform a function call to the software located at the handler identifier address which will then run and execute the received RF command. This is shown conceptually in FIG. 3B with arrow 357.

In this embodiment, lookup data structure 370 only contains the RF command identifiers for those new RF command handlers 374 stored in writable memory. Thus, if a match is not found within lookup data structure 370 then RF stack 358 will look for the RF command identifier within ROM 230 at 314 (FIG. 3A), such as by referencing a second lookup data structure stored within ROM 230. If the RF command identifier is located within ROM 230, then the identifier for the original RF command handler 360 will be retrieved and that command handler 360 will be called and/or used to execute the received RF command at 316. This is shown conceptually in FIG. 3B with arrow 359.

If a received RF command has separate handlers located within writable memory and ROM 230, then it is presumed that the handler located within writable memory is an upgraded or revised version and should be used to execute the received RF command instead of the handler stored in ROM 230. Thus, by referencing lookup data structure 370 stored in writable memory before referencing ROM 230, RF stack 358 will execute the received RF command with the handler identified within lookup data structure 370 at which point the process will terminate, leaving the prior handler version in ROM 230 unused.

Lookup data structure 370 can also be configured to include the command identifier and handler identifier for every RF command, regardless of where it is stored (e.g., FRAM 234, ROM 230, a hard disk, etc.). Such an approach has the benefit of reducing the number of locations that RF stack 358 must refer to in order to locate the proper handler, for example, RF stack 358 could avoid consulting a second lookup data structure in ROM 230.

Instead of including handler identifiers, lookup data structure 370 can instead include the handler software itself, at least for those RF commands that have new RF command handlers. Such a configuration would allow RF stack 358 to avoid the need to decode a handler identifier or redirect to a separate location in memory where the handler code is stored.

The term "data structure" is used herein, such as with respect to the lookup data structure, to broadly refer to any organization of data in software or in hardware that enables the organized data to be referenced by the application software. Examples of data structures include, but are not limited to, an array, a set, a tree, a software table, a software list, a record, a database, an object, a union, a hardware lookup table, or hardware lookup list. Lookup data structure 370 can also be implemented as a sequence of software instructions (e.g., as one or more software functions). It should be noted that, for ease of illustration, lookup data structure 370 is depicted as a human readable table in FIG. 4. Those of ordinary skill in the art will readily recognize that lookup data structure 370 would be implemented in machine-readable formats in actual implementations.

A first configuration key (e.g., start) 401 and a second configuration key (e.g., end) 403 can be included at the beginning and end of lookup data structure 370, as depicted in FIG. 4, to identify the boundaries of lookup data structure 370. Configuration key 401 can also be used to notify RF stack 358 whether any RF commands are present within lookup data structure 370. If RF stack 358 is executed from ROM 230, then in many embodiments RF stack 358 will automatically check lookup data structure 370 for revisions or updates to the handlers, e.g., by using a jump function. However, it is possible that there may not be any new or revised handlers identified within lookup data structure 370. For instance, in cases where the software code contained within ROM 230 was recently revised, there may not yet be a need to include further revised or supplemental RF command handlers. Configuration key 401 can therefore act as a flag telling RF stack 358 whether or not to reference lookup data structure 370.

In an example embodiment, configuration key 401 has a first predetermined value, which can be in the same format as the command and handler identifiers, e.g., 16 bit numbers. When RF stack 358 jumps to lookup data structure 370, it first checks the data contained within the configuration key 401 memory address to see if it matches the known predetermined code. If configuration key 401 does not match the predetermined code, then RF stack 358 knows that lookup data structure 370 is empty, or that there is otherwise no need to consult structure 370, and RF stack 358 proceeds to identify the received RF command by reference to the identifiers and/or handlers contained within ROM 230.

If configuration key 401 matches the predetermined code, then RF stack 358 can perform the comparison with the new RF command identifiers as previously explained. Configuration keys 401 and 403 preferably have the same value, which is different than those of the RF command identifiers. After progressing through the RF command identifiers, when the same predetermined code is read a second time RF stack 358 can realize that the second configuration key 403 has been reached indicating the end of lookup data structure 370. RF stack 358 can then reference the commands and/or handlers contained within ROM 230. Different predetermined codes can be used for configuration keys 401 and 403 instead of using the same codes.

Configuration key 403 and its location in lookup data structure 370 can also be used to deactivate or otherwise prevent the execution of certain handlers stored in writable memory. For example, during the manufacturing or factory programming process, it may be desirable to use certain RF commands to cause sensor control device 102 to take actions that may assist in its own programming, debugging, or testing. Examples of these "production" RF commands include, but are not limited to, those that instruct sensor control device 102 to report data read from memory (e.g., test program results, information confidential to the manufacturer, etc.), to write data (e.g., test patterns) or software (e.g., new handler software, etc.) to memory, and to execute a test routine.

Figure 4B:
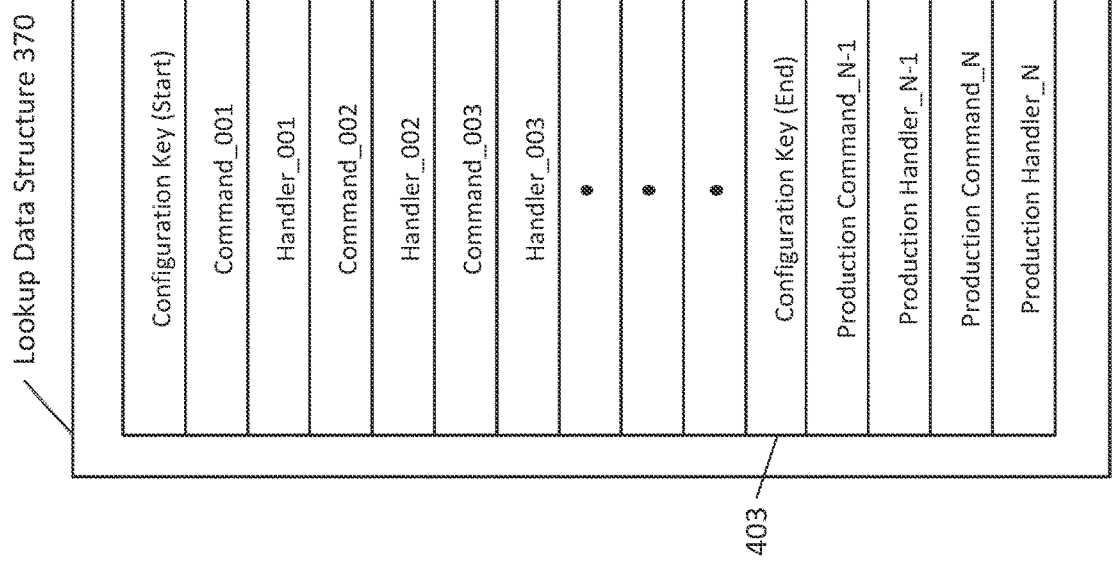

When sensor control device 102 is released from the manufacturer into the marketplace, it may be desirable to disable these production RF commands. In those embodiments, the command identifiers and the handler identifiers (or handlers themselves) can be grouped together near the sequential end (or higher address locations) of lookup data structure 370. This arrangement is depicted in FIG. 4B, where a group 410 of production-only commands are placed near the end of lookup data structure 370, with configuration key 403 located at the terminus of lookup data structure 370. Here, the "end" of lookup data structure 370 corresponds to the address(es) or memory location(s) that would be read last as the application software proceeds through lookup data structure 370, and the end-most address could be a numerically higher or lower address number as compared to the beginning of lookup data structure 370.

Figure 4C:
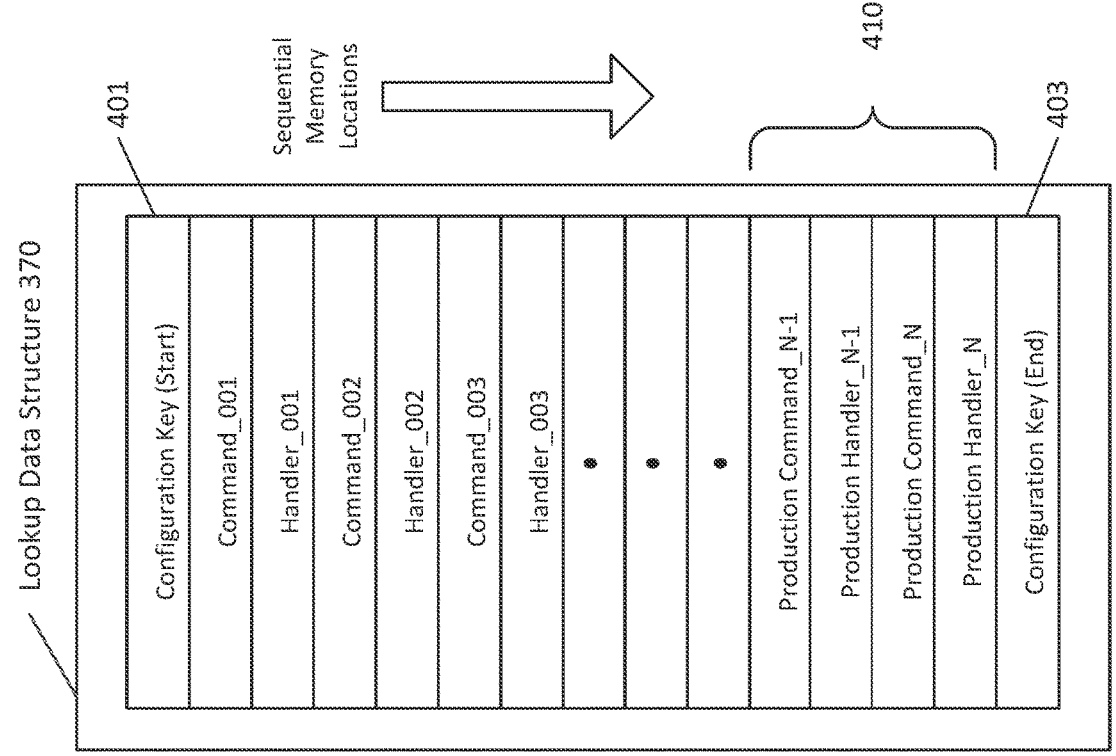

After production or manufacturing of sensor control device 102 is complete, disabling of these production RF commands can be achieved by writing configuration key 403 into a location 412 that would be read before group 410 as shown in FIG. 4C. As the application software reads through lookup data structure 370 it will interpret location 412 as the end of structure 370 and will not execute the RF command handlers contained in group 410, thereby preventing the execution of those commands from the writable memory while the device is in use in the field.

If the production RF commands are supported in the ROM, the production RF commands could still be executed from the ROM locations. In such an embodiment, the movement of configuration key 403 would only prevent execution of the RF command in whatever modified form is stored within the writable memory.

In alternative embodiments, multiple configuration keys 403 can be used to delineate group 410, such as by placement of a first configuration key 403 immediately before group 410 and a second configuration key immediately after group 410 (e.g., at the actual terminus of lookup data structure 370). In a production setting, the application software can be programmed to ignore the first configuration key 403 and to treat the second configuration key 403 as the actual terminus. But during actual use by the user (e.g., in the field), the application software can be programmed to treat the incidence of the first configuration key 403 as the effective terminus of lookup data structure 370.

Figure 5:
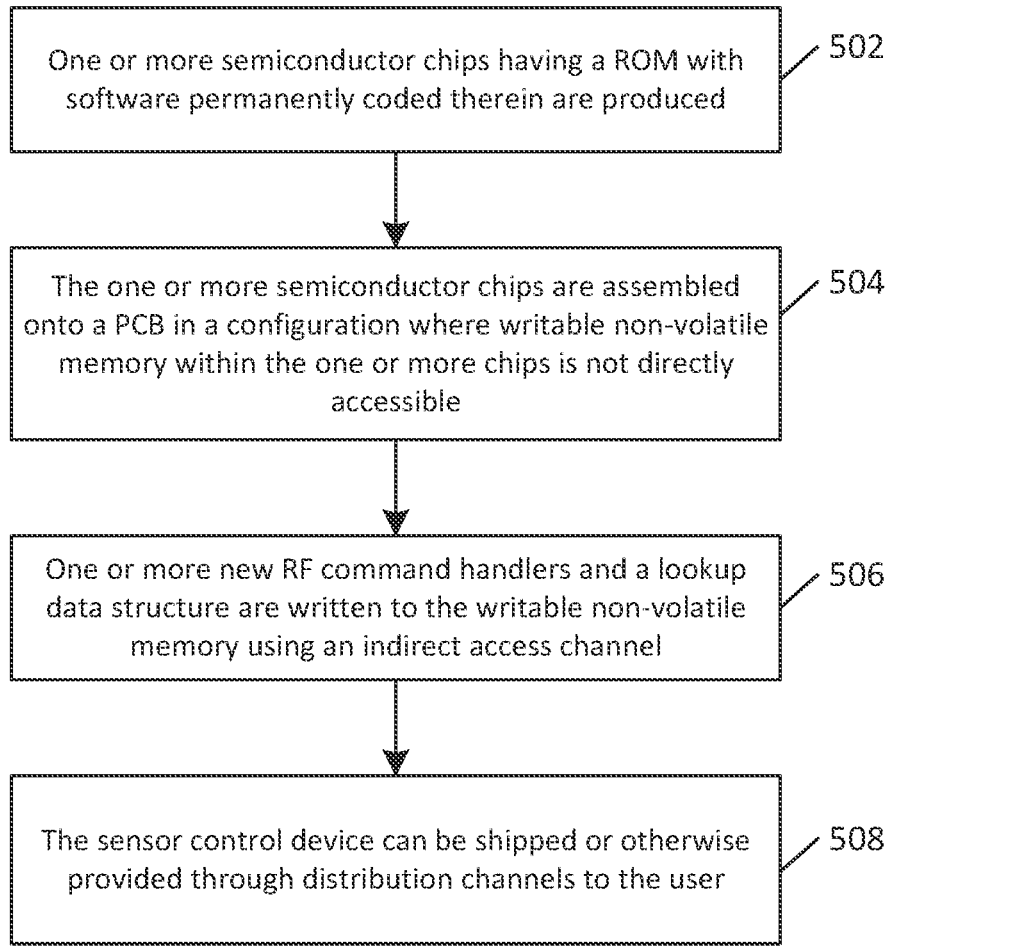
FIG. 5 is a flow diagram depicting an example embodiment of a method of producing a sensor control device having software stored in ROM and revised or updated RF command handling software stored in writable non-volatile memory.

Also provided herein are methods of manufacturing a sensor control device 102. FIG. 5 is a flow diagram depicting an example embodiment of one such method 500. At 502, one or more semiconductor chips having a ROM with software hardcoded therein are produced. At 504, the one or more semiconductor chips are assembled onto a PCB in a configuration where writable non-volatile memory resident within the one or more chips is not directly accessible, i.e., the memory bus and control signal leads are not present at an externally accessible interface. Then, at 506, one or more new RF command handlers and a lookup data structure are written to the writable non-volatile memory using an indirect access channel.

In one example embodiment, the indirect access channel is serial interface 229 (e.g., a boundary scan interface) that provides access to the memory bus and control signals for the writable non-volatile memory. In this embodiment, the new RF command handlers and lookup data structure are serially loaded into the serial interface and iteratively loaded into the memory so that they are available to be used for RF command execution, such as in embodiments of method 300 described herein.

In another example embodiment, the indirect access channel is an RF interface through communication circuitry 258. Here, the new RF command handlers and lookup data structure are transmitted over an RF wavelength to communication circuitry 258, which receives them and routes them to processor 256, or another programming unit, which can then write the received RF handlers and data structure to writable non-volatile memory.

The embodiments described herein can be integrated with analyte monitoring systems that function non-invasively, such as with the use of infrared (IR) energy, which does not require inserting a sensor device into biological matter while that matter is within the body. The embodiments described herein can also be integrated with analyte monitoring systems that utilize iontophoresis, such as in a non-invasive manner.

Generally, embodiments of the present disclosure are used with in vivo systems, devices, and methods for detecting at least one analyte, such as glucose, in body fluid (e.g., transcutaneously, subcutaneously within the ISF or blood, or within the dermal fluid of the dermal layer). In vivo analyte monitoring systems can be differentiated from "in vitro" systems that contact a biological sample outside of the body (or rather "ex vivo") and that typically include a meter device that has a port for receiving an analyte test strip carrying the biological sample of the user, which can be analyzed to determine the user's blood sugar level. Many in vitro systems require a "finger stick" to obtain the biological sample. In vivo analyte monitoring systems, however, can operate without the need for finger stick calibration.

Many embodiments include in vivo analyte sensors arranged so that at least a portion of the sensor is positioned in the body of a user to obtain information about at least one analyte of the body. However, the embodiments described herein can be used with in vivo analyte monitoring systems that incorporate in vitro capability, as well has purely in vitro or ex vivo analyte monitoring systems. Furthermore, the embodiments described herein can be used in systems, devices, and methods outside of the analyte monitoring field, either in other medical device fields, or any other field that requires the supply of power to one device from another.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method, comprising the steps of:
wirelessly receiving, by one or more processors of an analyte monitoring device, an RF command, wherein the analyte monitoring device comprises a transcutaneous sensor;
determining, by the one or more processors of the analyte monitoring device, if the received RF command is associated with a first command handler or a second command handler by reference to a lookup data structure, wherein the second command handler is a replacement for the first command handler;
executing, by the one or more processors of the analyte monitoring device, the received RF command by the second command handler if an identifier of the received RF command is in the lookup data structure; and
executing, by the one or more processors of the analyte monitoring device, the received RF command by the first command handler if the identifier of the received RF command is not in the lookup data structure.

2. The method of claim 1, wherein the first command handler is stored in a non-transitory read-only memory (ROM) with a permanently coded memory layout.

3. The method of claim 1, wherein the second command handler is stored in a non-transitory writable memory.

4. The method of claim 1, wherein the lookup data structure is stored in a non-transitory writable memory.

5. The method of claim 1, wherein the lookup data structure comprises an identifier for the second command handler and an identifier for the second RF command that is executable by the second command handler.

6. The method of claim 1, wherein the identifier for the second command handler is a memory pointer.

7. The method of claim 1, wherein the second command handler is capable of executing a new RF command not executable by the first command handler.

8. The method of claim 1, wherein the RF command is received over an RF communication path.

9. The method of claim 1, wherein the analyte monitoring device further comprises a non-transitory writable memory and a serial interface, and wherein the method further comprises the step of inputting the second command handler and the lookup data structure into the non-transitory writable memory through the serial interface.

10. A method, comprising the steps of:
wirelessly receiving, by one or more processors of an analyte monitoring device, an RF command, wherein the analyte monitoring device comprises a transcutaneous sensor;
determining, by the one or more processors of the analyte monitoring device, an appropriate command handler with which to execute the received RF command from among a first command handler and a second command handler, at least in part by comparing an identifier of the received RF command to identifiers in a lookup data structure, wherein the second command handler is a replacement for the first command handler;
executing, by the one or more processors of the analyte monitoring device, the received RF command by the second command handler if the identifier of the received RF command is in the lookup data structure; and
executing, by the one or more processors of the analyte monitoring device, the received RF command by the first command handler if the identifier of the received RF command is not in the lookup data structure.

11. The method of claim 10, wherein the first command handler is stored in a non-transitory read-only memory (ROM) with a permanently coded memory layout.

12. The method of claim 10, wherein the second command handler is stored in a non-transitory writable memory.

13. The method of claim 10, wherein the lookup data structure is stored in a non-transitory writable memory.

14. The method of claim 10, wherein the lookup data structure comprises an identifier for the second command handler and an identifier for the second RF command that is executable by the second command handler.

15. The method of claim 14, wherein the identifier for the second command handler is a memory pointer.

16. The method of claim 14, wherein the second command handler is capable of executing a new RF command not executable by the first command handler.

17. The method of claim 10, wherein the RF command is received over an RF communication path.

18. The method of claim 10, wherein the analyte monitoring device further comprises a non-transitory writable memory and a serial interface, and wherein the method further comprises the step of inputting the second command handler and the lookup data structure into the non-transitory writable memory through the serial interface.

* * * * *